(12) United States Patent
Chitre et al.

(10) Patent No.: US 7,383,091 B1
(45) Date of Patent: Jun. 3, 2008

(54) MEDICAL ELECTRICAL LEAD PROVIDING FAR-FIELD SIGNAL ATTENUATION

(75) Inventors: Yougandh Chitre, Valencia, CA (US); Xiaoyi Min, Thousand Oaks, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 468 days.

(21) Appl. No.: 10/656,649

(22) Filed: Sep. 4, 2003

Related U.S. Application Data

(60) Provisional application No. 60/476,472, filed on Jun. 5, 2003.

(51) Int. Cl.
*A61N 1/05* (2006.01)

(52) U.S. Cl. ...................... 607/127; 607/122

(58) Field of Classification Search ................ 607/120, 607/122, 123, 126, 127, 128; 600/375, 393, 600/374
See application file for complete search history.

(56) References Cited

U.S. PATENT DOCUMENTS

| | | | | |
|---|---|---|---|---|
| 4,892,102 A | | 1/1990 | Astrinsky | 128/642 |
| 5,306,292 A | | 4/1994 | Lindegren | 607/11 |
| 5,342,414 A | | 8/1994 | Mehra | 607/127 |
| 5,476,496 A | | 12/1995 | Strandberg et al. | 607/122 |
| 5,545,201 A | * | 8/1996 | Helland et al. | 607/127 |
| 5,645,580 A | | 7/1997 | Moaddeb et al. | 607/122 |
| 5,824,029 A | * | 10/1998 | Weijand et al. | 607/122 |
| 5,899,929 A | | 5/1999 | Thompson et al. | 607/28 |
| 6,321,123 B1 | | 11/2001 | Morris et al. | 607/122 |
| 6,978,178 B2 | | 12/2005 | Sommer et al. | 607/28 |
| 7,027,852 B2 | * | 4/2006 | Helland | 600/375 |
| 2002/0123784 A1 | | 9/2002 | Westendorp | 607/122 |
| 2003/0204232 A1 | | 10/2003 | Sommer et al. | 607/122 |
| 2005/0288761 A1 | | 12/2005 | Brabec et al. | 607/122 |

FOREIGN PATENT DOCUMENTS

WO WO03/092807 A1 11/2003
WO WO2006/012159 A1 2/2006

OTHER PUBLICATIONS

X. Min et al., "Computer Modeling and Experimental Validation on Effect of Bipolar Electrode Spacing on Near Field and Far Field Electrogram Amplitudes," *Computers in Cardiology*, IEEE 1999; vol. 26, pp. 201-204.
Restriction Requirement, mailed 10/06/2076: Related U.S. Appl. No. 10/656,649.

* cited by examiner

*Primary Examiner*—Kennedy J Schaetzle

(57) ABSTRACT

A bipolar pacing and sensing lead incorporates a range of active surface areas for each of the anode and cathode electrodes, and a range of inter-electrode spacings between the anode and cathode electrodes which, in combination, provide acceptable near-field signal amplitudes and attenuate the amplitudes of unwanted signals, such as far-field R-waves, far-field P-waves, and T-waves.

20 Claims, 2 Drawing Sheets

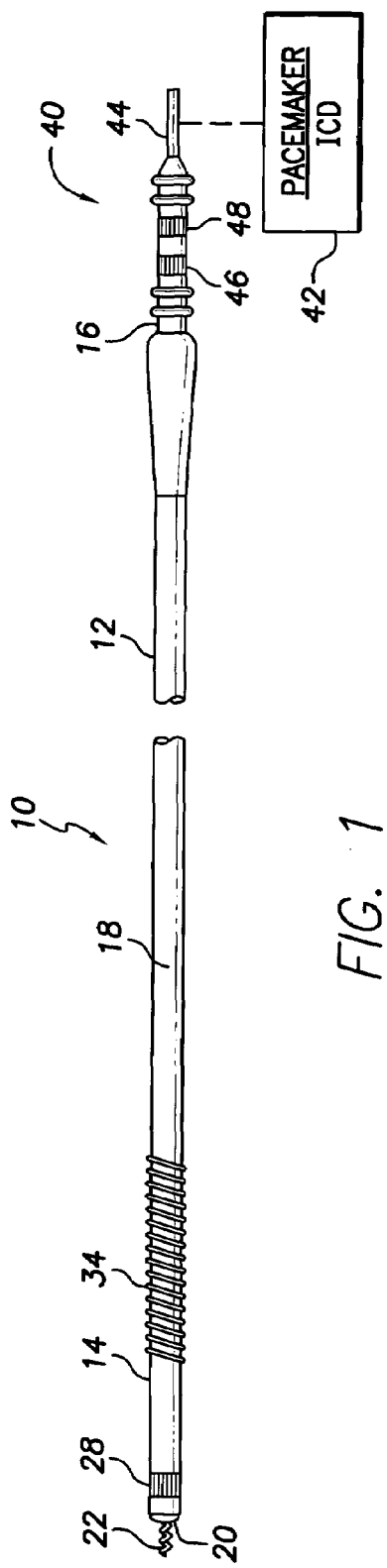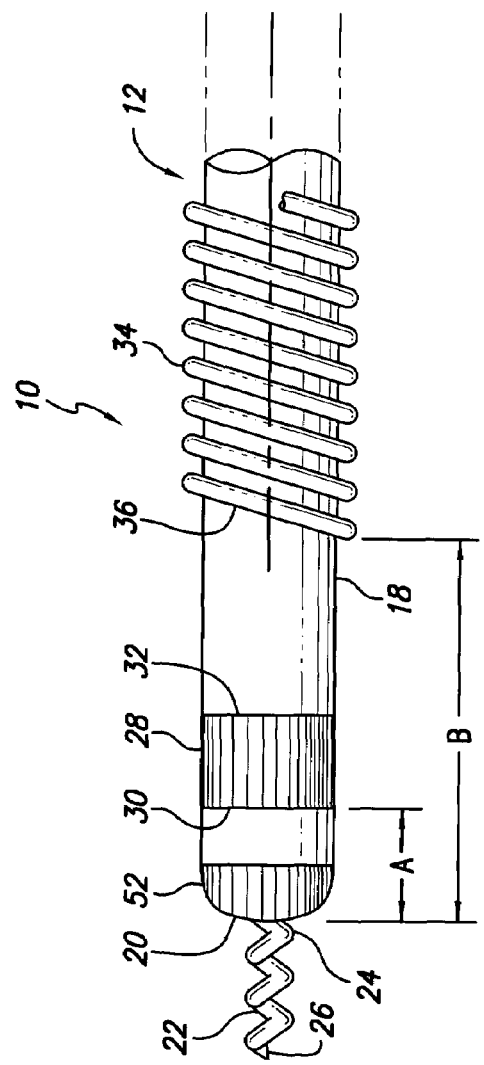

MEDICAL ELECTRICAL LEAD PROVIDING FAR-FIELD SIGNAL ATTENUATION

CROSS-REFERENCE TO RELATED APPLICATIONS

This application claims the benefit of U.S. Provisional Application No. 60/476,472, filed Jun. 5, 2003.

FIELD OF THE INVENTION

The present invention relates generally to implantable medical electrical leads and more particularly to bipolar pacing and sensing leads having electrodes arranged to suppress or attenuate undesirable signals, such as far-field signals and T-waves.

BACKGROUND OF THE INVENTION

Cardiac pacemaker lead systems fulfill two functions. The first function is to provide an electrical conduit by which a pacemaker output pulse is delivered to stimulate the local tissue adjacent to the distal tip of the lead. The second function is to sense local, intrinsic cardiac electrical activity that takes place adjacent to the distal tip of the lead.

One of the problems with such pacing and sensing lead systems is their inability to suppress or attenuate the voltage levels of far-field electrical signals. These signals are generated by depolarizations of body tissue in areas remote from the local sensing site and are manifested as propagated voltage potential wavefronts carried to and incident upon the local sensing site. A far-field signal may comprise an intrinsic or paced signal originating from a chamber of the heart other the one in which the lead electrodes are located. The sensing electrode(s) detect or sense the voltages of these far-field signals and interpret them as depolarization events taking place in the local tissue when such polarizations are above the threshold sensing voltage of the system. When far-field signal voltages greater than the threshold voltage are applied to the sensing circuitry of the pulse generator or pacemaker, activation of certain pacing schemes or therapies can be erroneously triggered.

With the development of universal stimulation/sensing systems, that is, three and four chamber combination pacemaker-cardioverter-defibrillators, accurate sensing of cardiac signals has become even more critical, and the management, suppression and/or elimination of far-field signals is vitally important to allow appropriate device algorithms to function without being confused by the undesirable far-field signals.

For a lead electrode implanted in the right atrium, the right ventricular R-wave comprises a far-field signal whose amplitude can easily swamp the smaller P-wave signal sought to be sensed. Thus, the discrimination of P-waves from the higher energy QRS complexes and particularly the R-wave spikes continues to present a formidable challenge.

Approaches to the problem of far-field signal sensing include configuring the circuitry of the pacemaker to attenuate far-field signals, and introducing a blanking period long enough to prevent the sensing of unwanted signals. These solutions are described in U.S. Pat. No. 4,513,752 assigned to the owner of the present invention.

The active surface areas of the electrodes and/or the interelectrode spacings in bipolar leads have been recognized to be of significance for various reasons, including far-field signal rejection or attenuation.

For example, U.S. Pat. No. 5,899,929 relates to a bipolar lead system for inducing ventricular tachycardia utilizing near-field T-wave sensing to determine the optimum parameters for anti-tachycardia stimulation, with the goal of accurately sensing the T-wave. U.S. Pat. No. 5,342,414 discloses a bipolar defibrillation lead for placement in the right ventricle. The lead is designed to place the defibrillation electrode as close to the apex of the right ventricle as practicable while retaining an adequately spaced bipolar (helical tip and ring) electrode pair for sensing the ventricular depolarizations. Thus, the ring electrode is located at the most distal extremity of the lead body permitting the proximal defibrillation electrode to be positioned correspondingly close to the lead's distal extremity. An interelectrode spacing of 5 mm between the distal end of the ring electrode and the proximal end of the active portion of the helical tip electrode is disclosed for adequate ventricular depolarization sensing. Electrode areas are not described and far-field signal rejection is not dealt with, let alone in the context of atrial pacing and sensing.

U.S. Patent Application Publication US2002/0123784A1 discloses a tri-polar pacing and sensing lead for use with an implantable medical device. The tri-polar lead includes three electrodes separated from each other to maximize sensing and pacing activities. A first ring electrode is located on the tri-polar lead within about 1.0 mm from a tip electrode. A second ring electrode is positioned on the tri-polar lead in the range of about 10.0 to 30.0 mm from the tip electrode. The electrode pair comprising the tip and first ring electrodes provides local sensing capabilities within either the atrium or the ventricle, while the electrode pair comprising the tip and second ring electrodes provides pacing capabilities. It will be seen that this tri-polar arrangement, although said to be capable of attenuating far-field pacing artifacts such as R-wave spikes which can contaminate sensing by an atrial lead, requires, in contrast to a bipolar lead, two pairs of electrodes to provide pacing and sensing and accordingly, requires a third electrical conductor to connect the additional ring electrode to the implantable medical device.

As illustrated by U.S. Pat. No. 5,476,496, the disclosure of which is hereby expressly incorporated by reference, it is known that in a bipolar pacing and sensing lead, the indifferent electrode (or anode), typically in the form of an electrically conductive ring disposed proximally of the tip cathode electrode, should have a large active surface area compared to that of the cathode. The objects of such an areal relationship are to reduce the current density in the region surrounding the anode so as to prevent needless or unwanted stimulation of body tissue around the anode when a stimulation pulse is generated between the cathode and anode, and to minimize creation of two focal pacing sites, one at the cathode and one at the anode which could promote arrhythmia. Typically, the total surface area of the anode is selected so as to be about two times to about six times that of the cathode.

Despite the advances in the field, there remains a need for a bipolar pacing and sensing lead with electrode parameters optimized to sufficiently attenuate far-field R-wave signals while at the same time providing clinically acceptable near-field P-wave signals for reliable sensing. Moreover, the need exists for such a lead that can be located in association with either the right ventricle or left ventricle, and that can sufficiently attenuate T-waves and far-field P-wave signals.

SUMMARY

Broadly, the present invention provides, in a bipolar pacing and sensing lead, a range of active surface areas for each of the anode and cathode electrodes, and a range of interelectrode spacings between the anode and cathode electrodes which, in combination, optimize both the sensed near-field signal and the ratio of the near-field to far-field signal amplitude, that is, the signal-to-noise ratio. The bipolar lead of the present invention in one embodiment is of the type having an electrically active, extendable/retractable screw-in helical tip electrode serving as a cathode and a proximal ring electrode functioning as an anode. The bipolar lead is suitable for either endocardial or epicardial placement.

In accordance with one specific, exemplary embodiment of the invention, there is provided an implantable medical electrical lead for transmitting electrical signals between an implantable medical device and cardiac tissue. The lead comprises a proximal end carrying a connector assembly connectable to the implantable medical device and a distal end carrying a ring electrode having a distal edge. The distal end of the lead further carries an extendible/retractable helical tip electrode electrically active along at least a portion thereof, for anchoring the distal end of the lead in the right atrium. The ring electrode has a surface area in the range of 10 to 40 mm$^2$, the helical tip electrode has an electrically active surface area in the range of 3.0 to 10 mm$^2$ and the spacing between the distal edge of the ring electrode and a proximal end of the at least active portion of the helical tip electrode being in the range of 1.0 to 8.0 mm, preferably 1.0 to about 3.5 mm.

More specifically, the ring electrode may have a surface area of 17 mm$^2$, the helical tip electrode may have an active surface area of 8.5 mm$^2$, and the spacing between the distal edge of the ring electrode and the proximal end of the at least active portion of the helical tip electrode may be on the order of about 1.07 mm.

Pursuant to an alternative embodiment of the invention, the helical tip electrode comprises a distal portion and a proximal portion, the distal portion comprising the electrically active portion of the tip electrode, and the proximal portion of the tip electrode being electrically insulating.

Optionally, a steroid collar may be disposed on the distal end of the lead between the ring electrode and a distal extremity of the lead.

Still further, a cardioverting-defibrillating electrode may be disposed on the distal end of the lead proximally of the ring electrode. The cardioverting-defibrillating electrode has a distal extremity, and that extremity may be spaced apart from a distal extremity of the lead by a distance in the range of 5 to 20 mm.

In another embodiment, the lead may include a cathode electrode in the form of a tip electrode, with the spacing between the tip electrode and the anodal ring electrode being between 1.0 and 8.0 mm, preferably 1.0 to about 3.5 mm. Furthermore, the lead is suitable for use in either the right atrium to attenuate far-field R-waves, or in either the left or right ventricle to prevent T-wave over-sensing and/or to attenuate far-field P-wave signals.

The foregoing electrode parameters optimize the pacing and sensing performance of a lead by providing clinically acceptable P-wave signal amplitudes while significantly attenuating R-wave far-field signals when implanted in the right atrium. In addition, in the case of a ventricular lead, the lead provides acceptable R-wave signal amplitudes and mitigates T-wave oversensing and attenuates far-field P-wave signals, without compromising autocapture and morphology discrimination. Further, the interelectrode spacing inhibits fibrotic encapsulation of the tip and ring electrodes and the consequent formation of a "virtual electrode". Such inhibition may be further enhanced by incorporating the steroid collar between the ring electrode and the distal extremity of the lead body. Still further, where a cardioverting-defibrillating electrode is included, the electrode parameters of the present invention permit it to be positioned closer to the ring electrode and thereby closer to the distal extremity of the lead body.

BRIEF DESCRIPTION OF THE DRAWINGS

The foregoing and other objects, features and advantages of the invention will be evident to those skilled in the art from the detailed description below, taken together with the accompanying drawings, in which:

FIG. 1 is side view of a bipolar pacing and sensing lead system incorporating one specific, exemplary embodiment of a lead in accordance with the present invention;

FIG. 2 is an enlarged side view of the distal end of the lead shown in FIG. 1;

DETAILED DESCRIPTION OF THE ILLUSTRATIVE EMBODIMENTS

Figure 3:
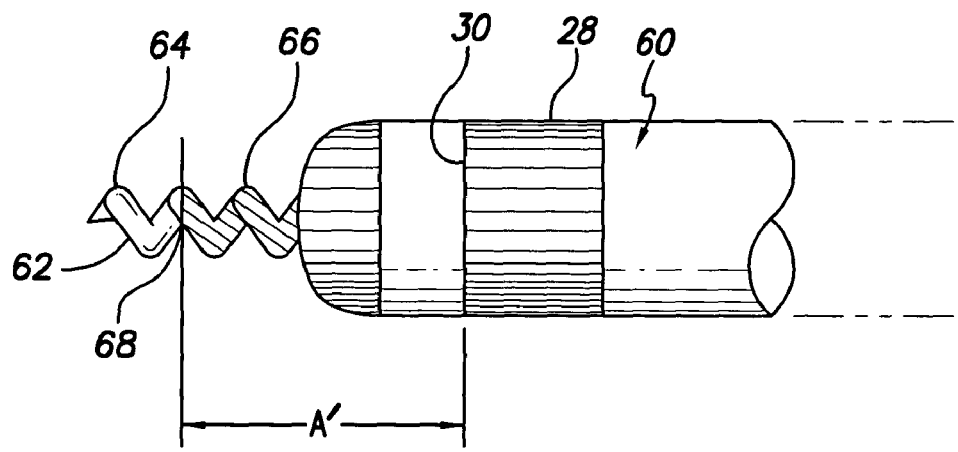
FIG. 3 is an enlarged side view of a portion of the distal end of a bipolar lead in accordance with an alternative embodiment of the invention.

The following description presents preferred embodiments of the invention representing the best mode contemplated for practicing the invention. This description is not to be taken in a limiting sense but is made merely for the purpose of describing the general principles of the invention whose scope is defined by the appended claims.

With reference to FIGS. 1 and 2, there is shown a bipolar pacing and sensing lead 10 in accordance with a preferred embodiment of the present invention for epicardial or endocardial placement in electrical contact with the heart. The lead 10 includes a lead body 12 comprising a distal end 14 and a proximal end 16 joined by a tubular sheath or housing 18 made of an insulating, biocompatible, biostable material such as silicone rubber or polyurethane.

The distal end 14 of the lead body 12 terminates at a distal extremity 20. The distal extremity 20 defines a central aperture through which a rotatable, helical screw-in tip electrode 22 may be extended to anchor the distal end 14 of the lead to adjacent cardiac tissue in the right atrium. The helical tip electrode 22 functions as a cathode and, in the embodiment of FIGS. 1 and 2, is electrically active along its entire length extending from the electrode's proximal end 24 at the distal extremity 20 of the lead body 12 to a distal tip 26.

Disposed along the distal end 14 of the lead body proximally of the distal extremity 20 is a sensing ring electrode 28 having a distal edge 30 and a proximal edge 32.

The lead body 12 may further carry a cardioverting-defibrillating electrode 34, which in one embodiment is in the form of an elongated coil wound about the outer surface of the insulating housing 18 and having a distal extremity 36. Alternately, cardioverting-defibrillating electrode 34 may be in the form of a conductive polymer electrode.

An interelectrode spacing "A" separates the distal edge 30 of the ring electrode 28 from the proximal end 24 of the helical tip electrode 22. A spacing "B" separates the distal extremity 36 of the cardioverting-defibrillating electrode 34 from the distal extremity 20 of the lead body.

The proximal end 16 of the lead 10 incorporates a connector assembly 40 for connecting the lead body 12 to a pacemaker and/or ICD 42. The connector assembly 40 includes a tubular, rotatable electrical pin terminal contact 44 and a pair of electrical ring terminal contacts 46 and 48. The connector assembly 40 of the lead is received within a receptacle of the pacemaker/ICD 42 and to prevent ingress of body fluids into the receptacle the connector assembly is provided with spaced sets of seals 50 (seals not depicted in FIG. 1) in accordance with well-known arrangements in the art.

The helical tip electrode 22 is mechanically and electrically connected to a coil conductor (alternatively a cable conductor) enclosed within the insulating lead body housing. The coil conductor is in turn coupled to the rotatable electrical pin contact 44 on the connector assembly 40 at the proximal end of the lead. The lumen of the tip electrode coil may provide a passage for a stylet or guidewire for steering and positioning the distal end 14 of the lead body during implantation.

The ring electrode 28 is electrically connected to one of the ring terminal contacts 46, 48 on the connector assembly by means of an electrical conductor within the lead body housing 18 that may be in the form of a coil or cable conductor. The cardioverting-defibrillating electrode 34 is electrically connected to the remaining one of the ring contacts 46, 48 also by means of, for example, a coil or cable conductor contained within the lead body housing 18. The various electrode conductors are, of course, individually insulated.

As shown in FIG. 2, the lead body 12 may optionally carry at the distal extremity thereof a steroid collar 52 interposed between the tip and ring electrodes 22 and 28 to mitigate fibrotic growth and the resulting fibrotic encapsulation of these electrodes. Preferably the proximal end of steroid collar 52 is closely spaced to the distal end of the ring electrode 28, for example on the order of a few tenths of millimeters apart. Alternatively, in place of steroid collar 52, the distal region of lead 10 may be dipped in a liquid solution containing a steroid to form a steroid-dipped distal region of lead. The steroid dip could cover a portion or all of ring electrode 28, or could be distal of ring electrode 28.

FIG. 3 shows a portion of a lead 60 in accordance with another embodiment of the invention. The lead 60 includes a helical, screw-in tip electrode 62, only a portion of which is exposed and electrically active. In this connection, the tip electrode 62 includes an uninsulated or bare distal portion 64 extending from an insulated proximal portion 66. The bare portion has a proximal extremity 68 separated from the distal edge 30 of the ring electrode 28 by an interelectrode spacing "A'". With the helical tip electrode 62 extended to anchor the distal end of the lead 60 in the adjacent atrial heart tissue, electrical contact will be established between the uninsulated distal portion 64 and the surrounding atrial tissue.

The present invention provides optimum bipolar atrial lead electrode parameters. More specifically, cathodal helical tip electrode 22 has an active surface area in the range of 3.0 to 10 mm$^2$, the anodal ring electrode 28 has an active surface area in the range of 10 to 40 mm$^2$, and the interelectrode spacing "A" (or "A'") between the distal edge 30 of the ring electrode 28 and the proximal extremity 24 (or 68) of the active portion of the helix tip electrode is in the range of 1.0 to 8.0 mm. More preferably, the interelectrode spacing "A" or "A'" between the tip and the ring electrodes is in the range of 1.0 to 3.5 mm. Most preferably, the helical tip electrode 22 has an active surface area of 8.5 mm$^2$, the ring electrode 28 has an active surface area of 17 mm$^2$, and the interelectrode spacing "A" or "A'" is 1.07 mm. In the interest of maintaining low capture thresholds, the surface area of the ring electrode should be at least 17 mm$^2$. The spacing "B" separating the distal end 36 of the cardioverting-defibrillating electrode 34 and the distal extremity 20 of the lead body is about 5 to 20 mm.

In one illustrative embodiment, the ratio of surface areas between anodal ring electrode 28 and cathodal helical tip electrode 22 is preferably between about 1.5:1 and about 3.0:1.

The foregoing electrode parameters optimize the pacing and sensing performance of the lead by providing clinically acceptable P-wave signal amplitudes while significantly attenuating R-wave far-field signals and mitigating T-wave oversensing without compromising autocapture and morphology discrimination. Further, the interelectrode spacing inhibits fibrotic encapsulation of the tip and ring electrodes and the consequent formation of a "virtual electrode". Such inhibition may be enhanced by incorporating a steroid collar between the ring electrode and the distal extremity of the lead body. Still further, where a cardioverting/defibrillating electrode is included, the electrode parameters of the present invention permit it to be positioned closer to the ring electrode and thereby closer to the distal extremity of the lead body.

Figure 4:
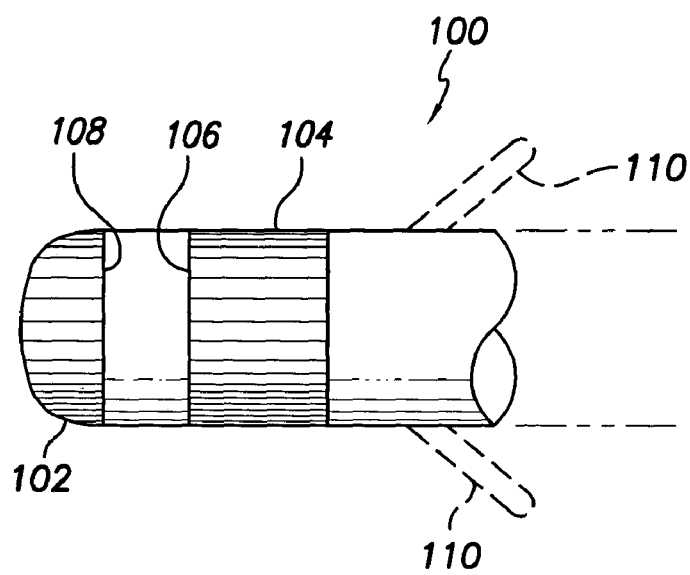
FIG. 4 is a side view of a distal end of a lead according to another illustrative embodiment.

FIG. 4 illustrates another embodiment of a lead 100, suitable for placement in either an atrium or a ventricle. Lead 100 includes a distal tip electrode 102 that serves as the cathodal electrode, and a proximal ring electrode 104 that serves as the anodal electrode.

As with the above-described embodiments, the cathodal tip electrode 102 has an active surface area in the range of 3.0 to 10 mm$^2$, the anodal ring electrode 104 has an active surface area in the range of 10 to 40 mm$^2$, and the interelectrode spacing between the distal edge 106 of the ring electrode 104 and the proximal edge 108 of tip electrode 102 is in the range of 1.0 to 8.0 mm. More preferably, the interelectrode spacing between the tip and the ring electrodes is in the range of 1.0 to 3.5 mm. Most preferably, the tip electrode 102 has an active surface area of 8.5 mm$^2$, the ring electrode 104 has an active surface area of 17 mm$^2$, and the interelectrode spacing "A" or "A'" is on the order of about 1.07 mm.

Lead 100 is suitable for placement in the atrium to sense near-field P-waves and to attenuate far-field R-waves (either intrinsic or paced R-waves). In addition, lead 100 is suitable for placement in the right ventricle or in the coronary sinus for placement adjacent the left ventricle. Due to the combination of the electrode spacing and relative surface areas, lead 100 is capable of preventing T-wave oversensing while providing clinically acceptable R-wave signal amplitudes. In addition, in some patients far-field P-wave oversensing can be problematic; lead 100 is capable of attenuating far-field P-waves (either intrinsic or paced P-waves) when placed in a patient's ventricle, in the same way lead 100 is capable of attenuating far-field R-waves when placed in the right atrium.

As will be readily understood by those skilled in the art, lead 100 may include passive fixation structure, for example one or more tines 110 (shown in phantom in FIG. 4), or may include an active fixation structure, such as an extendable helix similar to helix 22 shown in FIG. 1. The extendable helix would preferably be inactive in such an embodiment, and would serve merely to maintain the lead in position with tip electrode 102 in contact with the patient's tissue. In yet another embodiment, the active fixation structure may include a fixed helix, in other words a helix that permanently extends from the distal end of the lead and that is not retractable. Such active fixation structure is well known to those skilled in the art.

As described above, leads 10, 60, and 100 are suitable for use in either an endocardial or epicardial application. For example, lead 10 may be advanced through the patient's vasculature and into the right atrium, right ventricle, or coronary sinus, as is well known in the art. Alternatively, lead 10 may be advanced through an incision made in the patient's side until the distal tip of lead 10 engages the desired endocardial tissue, for example the myocardial tissue outside the left ventricle.

While several illustrative embodiments of the invention have been shown and described, numerous variations and alternative embodiments will occur to those skilled in the art. Such variations and alternative embodiments are contemplated, and can be made without departing from the spirit and scope of the invention.

What is claimed is:

1. An implantable medical electrical lead for transmitting electrical signals between an implantable medical device and cardiac tissue and configured to significantly attenuate far-field and repolarization signals, the lead comprising:
   a lead body defining a proximal end comprising a connector assembly configured for connection to the implantable medical device, the lead body further defining a distal region; and
   a helical tip electrode extending from the distal region and a second electrode spaced proximally from the tip electrode, the second electrode having a surface area in the range of 14 to 40 mm$^2$, the helical tip electrode having an active surface area in the range of 3.0 to 10 mm$^2$ and the spacing between the second electrode and the helical tip electrode being in the range of 1.0 mm to about 3.5 mm.

2. The lead of claim 1 wherein the helical tip electrode is extendable and retractable relative to the distal region of the lead.

3. The lead of claim 1 wherein the second electrode comprises a ring electrode.

4. The lead of claim 1 wherein the helical tip electrode comprises a distal portion and a proximal portion, the distal portion comprising the electrically active portion of the tip electrode, and the proximal portion of the tip electrode being electrically insulating.

5. The lead of claim 1 further comprising:
   a steroid disposed on the distal region of the lead.

6. The lead of claim 1 further comprising:
   a cardioverting-defibrillating electrode disposed on the distal end of the lead proximal to the second electrode.

7. The lead of claim 6 wherein the cardioverting-defibrillating electrode is spaced from a distal extremity of the lead by a distance in the range of between about 5 and about 20 mm.

8. The lead of claim 1, wherein the lead body is configured for placement in the right atrium.

9. The lead of claim 1, wherein the lead body is configured for placement in at least one of a ventricle and a coronary sinus.

10. An implantable medical electrical lead for transmitting electrical signals between an implantable medical device and cardiac tissue and configured to significantly attenuate far-field and repolarization signals, the lead comprising:
    a lead body defining a proximal end comprising a connector assembly configured for connection to the implantable medical device, the lead body further defining a distal region;
    a helical tip electrode extending from the distal region, and a second electrode spaced proximally from the helical tip electrode and connected to the lead body, the second electrode having a surface area in the range of 10 to 40 mm$^2$, the helical tip electrode having an active surface area in the range of 3.0 to 10 mm$^2$ and the spacing between the second electrode and the helical tip electrode being in the range of 1.0 mm to about 3.5 mm.

11. The lead of claim 10 wherein the helical tip electrode is extendable from the distal end of the lead.

12. The lead of claim 11 wherein the helical tip electrode comprises a distal portion and a proximal portion, the distal portion comprising an electrically active portion of the tip electrode, and the proximal portion of the tip electrode being electrically insulating.

13. The lead of claim 10 further comprising:
    a steroid disposed on the distal end of the lead distal to the second electrode.

14. The lead of claim 10 further comprising:
    a cardioverting-defibrillating electrode disposed on the distal end of the lead proximal to the second electrode.

15. An implantable medical electrical lead for transmitting electrical signals between an implantable medical device and cardiac tissue and configured to significantly attenuate far-field and repolarization signals, the lead comprising:
    a lead body defining a proximal end comprising a connector assembly configured for connection to the implantable medical device, the lead body further defining a distal region;
    a helical tip electrode extending from the distal region, and a second electrode spaced proximally from the helical tip electrode and connected to the lead body, the second electrode having a surface area in the range of 14 to 40 mm$^2$, the helical tip electrode having an active surface area in the range of 3.0 to 10 mm$^2$ and the spacing between the second electrode and the helical tip electrode being in the range of 1.0 mm to about 3.5 mm.

16. The lead of claim 15 wherein the helical tip electrode is extendable and retractable relative to the distal region of the lead.

17. The lead of claim 15 wherein the helical tip electrode comprises a distal portion and a proximal portion, the distal portion comprising the electrically active portion of the tip electrode, and the proximal portion of the tip electrode being electrically insulating.

18. The lead of claim 15 further comprising:
    a steroid disposed on the distal region of the lead.

19. The lead of claim 15, wherein the lead body is configured for placement in the right atrium.

20. The lead of claim 15, wherein the lead body is configured for placement in at least one of a ventricle and a coronary sinus.

* * * * *